United States Patent [19]
Butuzov et al.

[11] Patent Number: 5,891,106
[45] Date of Patent: Apr. 6, 1999

[54] SYRINGE

[75] Inventors: Valentin Sergeevich Butuzov; Igor Alexandrovich Chougailov, both of Moscow, Russian Federation

[73] Assignee: Medinfodent Ltd., Moscow, Russian Federation

[21] Appl. No.: 849,326

[22] PCT Filed: Dec. 4, 1995

[86] PCT No.: PCT/RU95/00261

§ 371 Date: Jun. 3, 1997

§ 102(e) Date: Jun. 3, 1997

[87] PCT Pub. No.: WO96/17640

PCT Pub. Date: Jun. 13, 1996

[30] Foreign Application Priority Data

Dec. 9, 1994 [RU] Russian Federation ............. 9404247I

[51] Int. Cl.⁶ .................................................. A61M 5/00
[52] U.S. Cl. ........................................... 604/209; 604/232
[58] Field of Search ..................... 604/209, 208, 604/218, 239, 240, 242, 243, 272, 232

[56] References Cited

U.S. PATENT DOCUMENTS 4,710,172 12/1987 Jacklich et al. ..................... 604/209 X
4,710,178 12/1987 Leonard et al. ........................ 604/209
4,936,833 6/1990 Sams ..................................... 604/232
5,433,352 7/1995 Ronvig ................................ 604/209 X

*Primary Examiner*—John D. Yasko
*Attorney, Agent, or Firm*—Frishauf, Holtz, Goodman, Langer & Chick, P.C.

[57] ABSTRACT

A syringe having a body connected with a barrel and a fastening unit for fastening of the double-edged needle at the other end. A plunger having ratchet teeth is located in the body. A stopper pawl which prevents return movement of the plunger is installed with a possibility of interaction with the plunger. A drive unit including a rotary handle is fixed on the body and a drive pawl is fixed on the handle. A compensator of a cartridge length is located in the body. A guiding element is positioned between the barrel and the fastening unit. The fastening unit is made in the form of a hollow sphere with a slot and a holder of double-edged needle which is fixed in the slot with the possibility of moving in the slot on the generatrix of a surface of the sphere to an angle up to 180°. An aspiration element is fixed on one end of the plunger. The stopper pawl is installed in the body under the rotary handle behind the drive pawl and the stopper pawl and the drive pawl are fixed with a possibility of runaway from meshing the plunger with the help of the rotary handle. Another end of the plunger is provided with a rest for a finger.

5 Claims, 3 Drawing Sheets

SYRINGE

This application is a 371 of PCT/RU95/00261 filed Dec. 4, 1995

1. Technical Field

This invention relates to a medical instruments and specifically to devices and apparatuses for introducing of medical preparations in a process of therapeutical and/or surgical treatment. More specifically the invention relates to a structure of a syringe and can be used, in particular, at dental treatment while providing for intraligamental, intrabonal, intraseptal or endopulpier analgesia, as well as for sealing of root channels of teeth.

Particularly, the invention relates to particulars of syringe details such as a drive unit ensuring strictly dosed and limited movement of a plunger by its blocking; a fastening unit for double-edged needle ensuring mobility of injection part of the needle; as well as to their mutual arrangement and other elements, ensuring simplicity, reliability and universality of the syringe.

2. Background Art

One has to deal in dental treatment with a patient who often suffers a notable pain from the beginning. Therefore there is the need to provide the effective local analgesia at the very beginning of a medical (therapeutical or surgical) interference.

Generally a structure of a syringe used in dental treatment contains a joint casing (a body and a barrel), in which a cartridge with appropriate analgesic means is placed, usually having an elastic face wall on the part of a needle and on the other part—a movable plug interacting with a plunger located coaxial in the back part of the casing. A mechanical drive provides for longitudinal translational motion of the plunger. Such structure is described, for example, in French application FR 2343486, published in 1977. IPC A 61 M May 20.

Exact dosage of an analgesic substance is extremely important when highly efficient medical means are used for to exclude pain feelings of the patient on the one hand, and to prevent excessive introduction (overdosing) of the analgesic on the other. Exact dosing is especially desirable at intraligamental, intrabonal, intraseptal or endopulpier analgesia. In the state of the art such dosing is provided by providing for the structure of a syringe, having a joint casing in which above mentioned cartridge interacting with the plunger is placed, of a ratchet-and pawl mechanism for fixed movement of the plunger. The ratchet-and pawl mechanism includes the plunger provided by ratchet teeth, and a syringe drive system actuated by a handle hinged to the casing, which can be squeezed with the casing by a hand of the dentist carrying out an analgesia.

The closest analogue to the claimed device is a dental syringe, which consists of a body, connected by a bayonet joint with a barrel, a piston with a plunger having ratchet teeth, and a drive system, including a rotary handle fixed on the body, a driver pawl interacting with the handle by means of a rotary lever with a roller, and a sleeve with a bushing having ledges and loaded by a spring.

A lock for preventing the return move of the plunger, which is made in a form of a cylinder with ledges interacting with the ratchet teeth, is rigidly fixed in the sleeve by means of a pin. The lock permits the plunger to be moved in the direction to the barrel only. A cartridge is placed into the barrel, which has an elastic end wall on the one hand, and movable plus interacting with a piston - on the other. There is a needle inside the barrel, piercing the end wall of the cartridge. For fastening of the infection needle the barrel is provided by a bevel (USSR inventor's certificate SU 1591989. IPC A 61 M May 24, 1988).

This structure permits to inject the analgesic liquid by exact dozes, corresponding to movement of the cartridge piston to a distance equal to the step of the ratchet tooth on the plunger. However in some cases there is the need to inject significant quantity of the analgesic liquid in a mode of conducting or infiltration analgesia. Such necessity can be found out after the analgesic treatment already began, that in the known state of the art would require extraction of the needle from the patient's gum and replacement of the dosing syringe to a conventional one having the back end of the plunger interacting with the cartridge piston provided by a rest for a finger of the dentist.

It should be noticed also, that in the course of a local analgesia there is the necessity to apply a return move of a piston (aspiration test) for the purpose of exception of placing of the injection needle in a blood vessel.

However the state of the art does not permit to execute the aspiration test during the local analgesia using the cartridges and the dosing injection of a medical substance.

Also the state of the art does not permit to execute the local analgesia in distal jaw departments without deformation of a working part of the injection needle.

DISCLOSURE OF INVENTION

An aim of this invention is to provide a syringe using cartridges with a medical means and enabling to execute the dosing intraligamental as well as the conducting analgesia.

Another aim of the invention is the creation of a syringe which additionally enables the aspiration test in the mode of conducting analgesia.

A further aim of the invention is to provide a possibility to control the position of the injection needle in the course of intraligamental, intraseptal and other infections in distal jaw departments without deformation of the working part of the needle.

These and other objects are achieved by a syringe containing a body connected with a barrel which other end having a unit for fastening of the double-edged needle, a plunger having ratchet teeth and located in the body, a stopper pawl of return move of the plunger, installed with a possibility of interaction with the plunger, a drive unit, consisting of a rotary handle fixed on the body and a drive pawl fixed on the handle, compensator of a cartridge length, located in the body, a guiding element, positioned between the barrel and the unit for fastening of the double-edged needle, which unit is made in the form of a hollow sphere with a slot and a holder of the double-edged needle fixed in the slot with the possibility of moving in the slot on the generatrix of the surface of the sphere to an angle up to 180°, an aspiration element, fixed on the one end of the plunger, wherein the stopper pawl of return move of the plunger is installed in the body under the rotary handle behind the drive pawl; the stopper pawl of return move and the drive pawl are hinged with the possibility of runaway from meshing the plunger with the help of the rotary handle; another end of the plunger provided by a rest for a finger of the dentist; and the aspiration element is made in a spear like or mushroom like form; the spear like aspiration element is made slitted in the axis; the aspiration element is made removable.

Providing the syringe by the aspiration element permits to prevent the radial displacement of the end of the plunger and consequently to prevent destruction of cartridge walls, as well as to execute the aspiration test.

The mushroom like aspiration element should be used in case of using the cartridges, which plug-pistons have a cylindrical recess. It provides for gripping effect when penetrating in the recess by its "umbrella", which diameter shall be more than the diameter of the recess; that permits to execute return movement of the plug-piston. The spear like aspiration element should be used for the cartridges without the recess in the piston; the spear like aspiration element may be made slitted and executer from elastic material with a large module of elasticity for more effective gripping as far as the plug-pistons are manufactured of materials of various hardness.

The drive unit, consisting of the rotary handle, the driver pawl and the stopper pawl of return move, permits to execute the dosing introduction of a medical preparation under a large pressure, as well as permits to make the conducting analgesia by runaway the driver pawl and the stopper pawl of return move from meshing the plunger.

The compensator of the cartridge length is provided, for example, by a spring and a squeezing bushing; it serves for fixing the cartridge as well as for prevention its axial moving at aspiration process.

The unit for fastening of the double-edged needle is made in the form of hollow sphere with the meridian slot, in which the holder of double-edged needle is fixed with the possibility of moving in the slot on the generatrix of the surface of the sphere to an angle up to 180°, and the guiding element is positioned in the section of the sphere between the unit for fastening of the double-edged needle and the barrel. The guiding element "catches" the needle back nose and prevents deformation of the cartridge membrane, which otherwise could lead to leakage of the analgesic liquid under the pressure.

Figure 1:
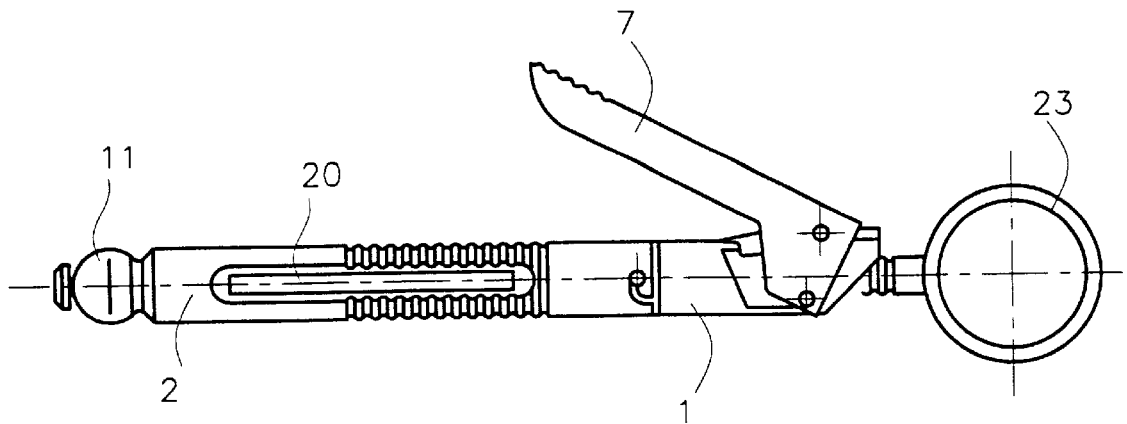
FIG. 1 represents the general view of the syringe according to the claimed invention.
Figure 4:
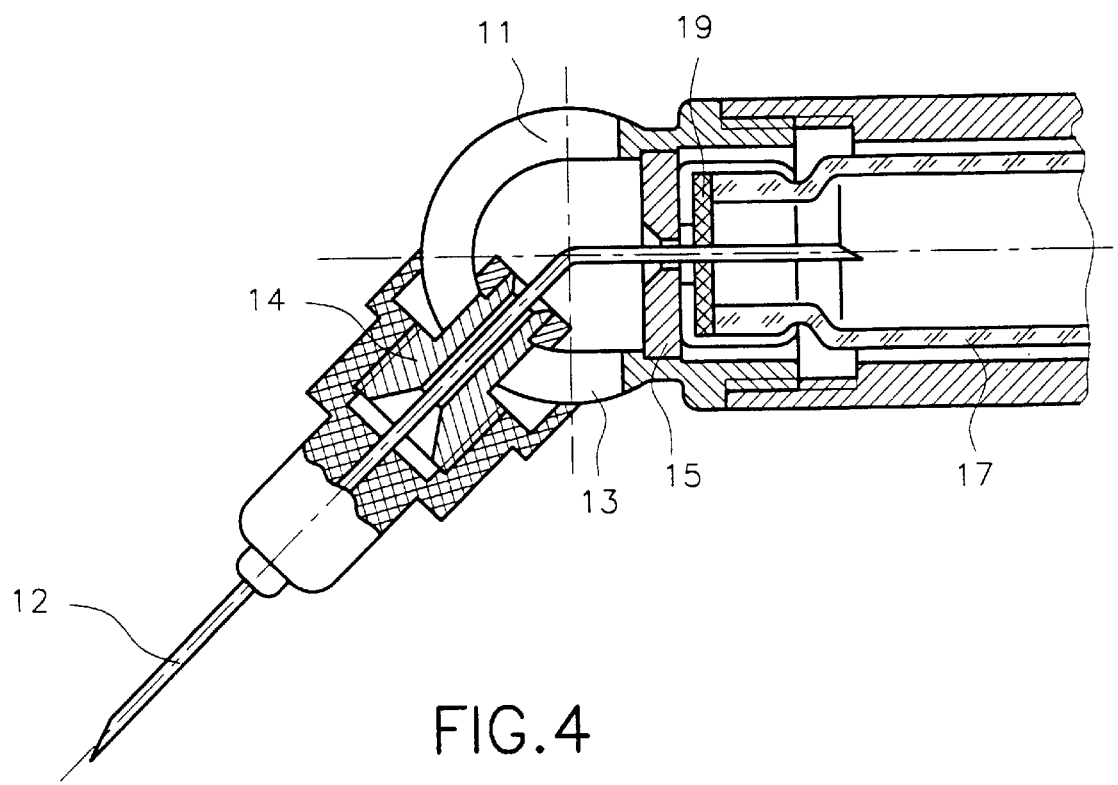
FIG. 4 is the cross-section of the unit for fastening of the double-edged needle together with that needle in the working position.
Figure 2:
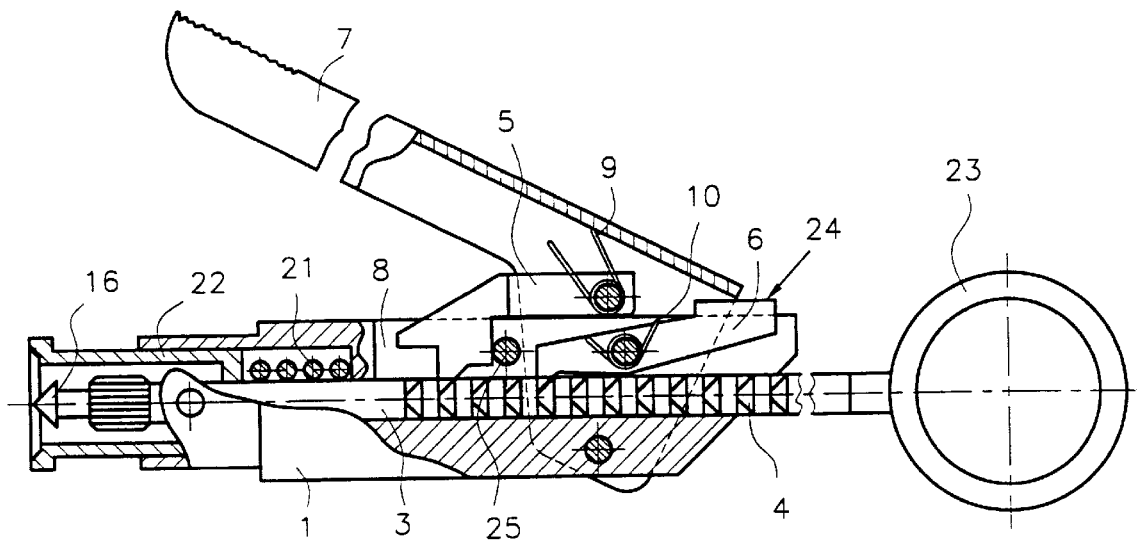
FIG. 2 represents the general view of the drive unit in working position for the mode of dosing introduction of the analgesic liquid.
Figure 3:
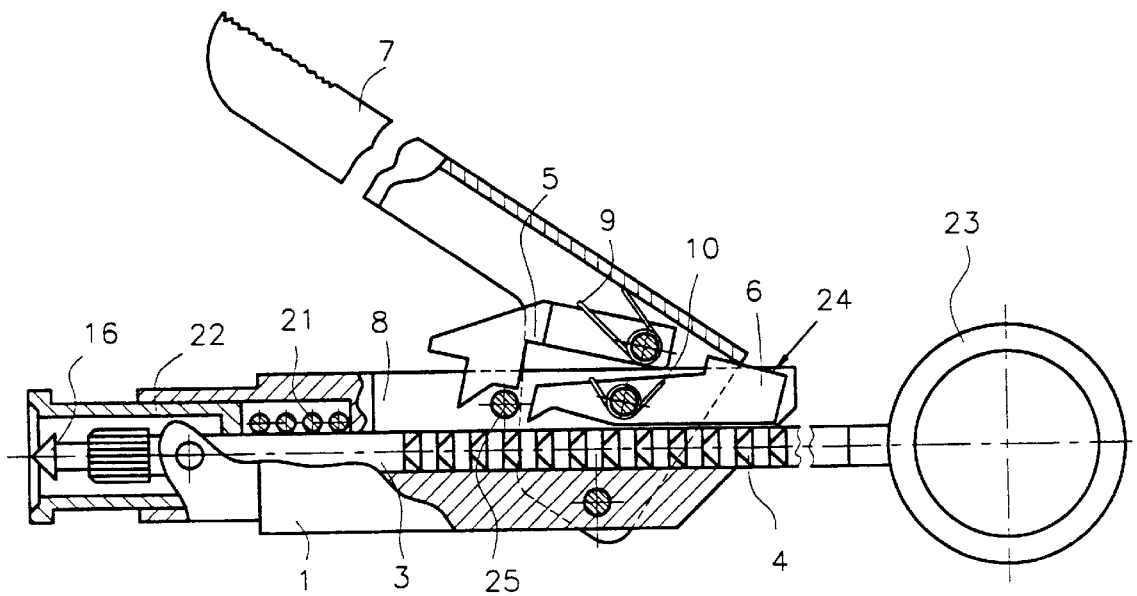
FIG. 3 represents the general view of the drive unit in working position for the mode of free introduction of the analgesic liquid.
Figure 5:
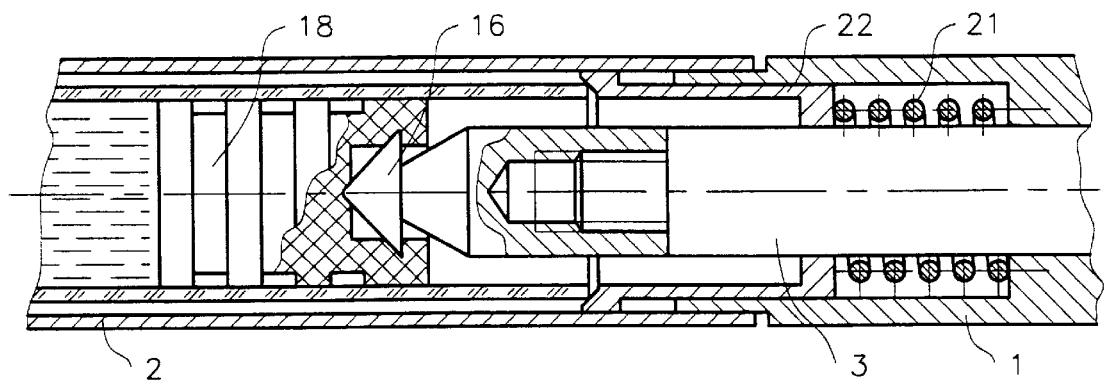
FIG. 5 is the variant of gripping (fixing) of the plunger with the cartridge piston for one type of the plugs.
Figure 6:
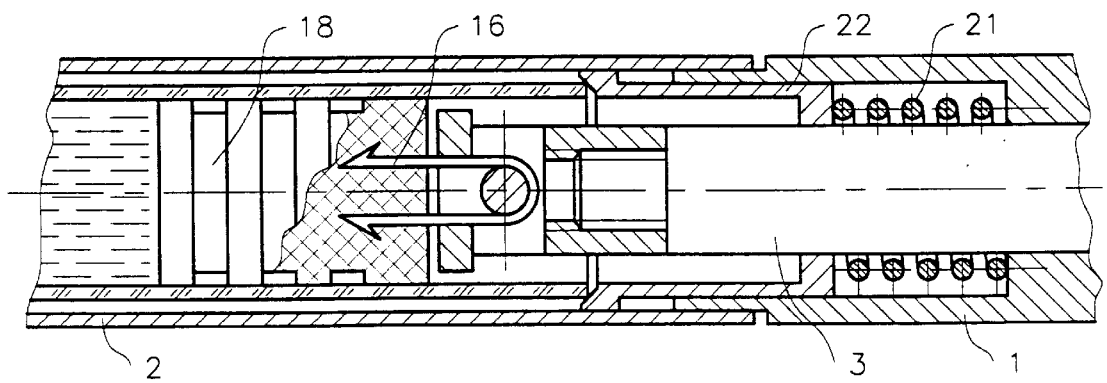
FIG. 6 is the variant of gripping (fixing) of the plunger with the cartridge piston for other type of the plugs.

The following reference signs are used in the drawings:
1—the body of the syringe;
2—the barrel of the syringe;
3—the plunger;
4—the ratchet teeth on the plunger;
5—the driver pawl of the plunger;
6—the stopper pawl of return move of the plunger;
7—the rotary handle;
8—the longitudinal slot in the back part of the body for the driver pawl and the stopper pawl of return move;
9—the first resilient element, interacting with the driver pawl and with the handle;
10—the second resilient element, interacting with the stopper pawl of return move and with the back part of the body of the syringe;
11—the sphere like unit for fastening of the double-edged needle;
12—the double-edged needle;
13—the slot in the sphere like fastening unit 11;
14—the holder of the double-edged needle 12;
15—the guiding element for the double-edged needle 12;
16—the aspiration element of the plunger;
17—the cartridge with medical means;
18—the piston of the cartridge 17;
19—the elastic membrane of the cartridge 17;
20—the slot in the barrel 2 of the syringe for the visual control of the charge of an analgesic liquid;
21—the spring of the compensator of the cartridge length;
22—the squeezing bushing of the compensator of the cartridge length;
23—the rest for a finger of the dentist on the end of the plunger 3;
24—the platform on the back end of the stopper pawl of return move, interacting with the handle;
25—the fixing pin of the driver pawl.

BEST MODE FOR CARRYING OUT THE INVENTION

According to the best mode for carrying out the invention illustrated by the drawings, a syringe includes body 1 and barrel 2. Plunger 3 having ratchet teeth 4 is located in the body 1. Driver pawl 5 and stopper pawl of return move 6 interact with the ratchet teeth of the plunger. The driver pawl 5, which is hinged to rotary handle 7, is installed with the possibility of interaction with the ratchet teeth 4 of the plunger 3 through longitudinal slot 8 in the body 1 and is spring-loaded with respect to the handle 7 by the first resilient element 9. The stopper pawl of return move 6, which is hinged to the body 1, is installed with the possibility of interaction with the ratchet teeth 4 of the plunger 3 through the same longitudinal slot 8 in the body 1 behind the driver pawl and is spring-loaded in respect of the body 1 by the second resilient element 10.

Unit 11 for fastening of double-edged needle 12, which is located on the forward end of the barrel 2, is designed in the form of a sphere having meridian slot 13, and holder 14 of the double-edged needle 12, which is protruded through the slot 13 with the possibility of moving along the slot practically up to 180°. Guiding element 15 is installed in the section of the sphere for fixing the radial position of that end of the double-edged needle 12 which penetrates into cartridge 17. Aspiration element 16 is connected with the forward part of the plunger 3.

For preparation of the syringe to work, the cartridge 17 with an analgesic liquid is placed into the hollow barrel 2. The cartridge 17 is closed on the part of the plunger 3 by plug-piston 18, and on the part of the double-edged needle 12 —by membrane 19. There is slot 20 in the wall of the forward part of the barrel 2 for a visual control of the analgesic liquid. A compensator consisting of spring 21 and squeezing bushing 22 is installed inside the body 1. The back end of the plunger 3 is finished by rest 23 for a finger of the dentist. One installs the holder 14 on the axis of the syringe, enters the double-edged needle 12 by its back (non-injecting) end through the holder 14 and through the guiding element 15, piercing elastic wall (membrane) 19 of the cartridge 17. Then the injection end of the needle 12 can be installed with any inclination in respect of the axis of the syringe, necessary for the injection, by moving of the holder 14 in the meridian slot 13. A grade scale can be put on the sphere along the slot for convenience of choice of an angle of inclination of the needle. During that move the radial position of the opposite end of the needle is fixed by the guiding element 15 to prevent a deformation of the membrane of the cartridge.

In the mode of intraligamental analgesia the syringe according to the invention works as follows. After the introduction of the needle in a periodontal cavity, the handle 7 shall be squeezed, this move through the first resilient element 9 is transmitted to the driver pawl 5, and from the driver pawl 5—to the plunger 3. Each squeezing results in the moving ahead of the plunger 3 on a length of one ratchet tooth 4 and in the influencing through the aspiration element 16 on the plug-piston 18, thus providing the dosing introduction of an analgesic. The stopper pawl of return move 6 is engaged with the ratchet teeth 4 simultaneously with the driver pawl 5, thus blocking the return move of the plunger 3. Being free (i.e. without the pressure of a hand of the dentist, the first resilient element 9 is placed in a neutral position providing for the squeezing of the driver pawl 5 with the plunger 3, engagement with the ratchet teeth 4 of the plunger 3 and squeezing out of the handle 7 from the body 1 up to its rest on a platform 24 on the back end of the stopper pawl of return move. The second resilient element 10 is also placed in a neutral position providing for the squeezing of the stopper pawl of return move 6 with the plunger 3 and engagement with the ratchet teeth 4 of the plunger 3. Thus, with each squeezing of the handle 7, the plunger 3 is moved ahead on the length of one ratchet tooth 4; the move of the plunger 3 is transmitted through the aspiration element 16 to the plug-piston 18, thus enabling the dosing introduction of the analgesic.

For a transfer the syringe in the mode of free dosing, the handle 7 shall be squeezed out from the body to a position which is farther than the free one, thus the first resilient element 9 removes the driver pawl 5 from the meshing with the ratchet teeth 4 of the plunger 3; the driver pawl being fixed by the fixing pin 25 which is located on the body. The handle 7 when squeezing out presses the platform 24 on the back end of the stopper pawl of return move 6, also removing it from the meshing with the teeth 4 of the plunger 3, which shall be removed in the last position on the right. Thus the syringe is transferred to the mode of free dosage of a medical means by pressing the rest 23 by a finger of the dentist.

INDUSTRIAL APPLICABILITY

This invention relates to medical instruments and can be used as a syringe of a universal type for effecting all modes of local analgesia at disease treatment.

The syringe according to the invention, which permits to carry out the intraligamental, intrabonal, intraseptal and other analgesia, is particularly suitable when highly effective medical means of a minimum dosage are used.

We claim:

1. A syringe including a body connected with a barrel, which other end having a fastening unit for fastening of a double-edged needle, a plunger having ratchet teeth and located in the body, a stopper pawl which prevents return movement of the plunger, installed with a possibility of interaction with the plunger, a drive unit including a rotary handle, fixed on the body, and a drive pawl fixed on the handle, characterized in that:

a compensator of a cartridge length is located in the body;

a guiding element is positioned between the barrel and the fastening unit;

which fastening unit is made in the form of a hollow sphere with a slot and a holder of double-edged needle fixed in the slot with the possibility of moving in the slot on the generatrix of a surface of the sphere to an angle up to 180°;

an aspiration element is fixed on one end of the plunger;

the stopper pawl of the plunger is installed in the body under the rotary handle behind the drive pawl; and the stopper pawl and the drive pawl are fixed with a possibility of runaway from meshing the plunger with the help of the rotary handle, and wherein another end of the plunger is provided with a rest for a finger.

2. The syringe according to claim 1, wherein the aspiration element is spear like.

3. The syringe according to claim 2, wherein the spear like aspiration element is slit along an axis thereof.

4. The syringe according to claim 1, wherein the aspiration element is mushroom like.

5. The syringe according to claim 1, wherein the aspiration element is removable.

* * * * *